United States Patent [19]

Winicov

[11] Patent Number: 5,616,348

[45] Date of Patent: *Apr. 1, 1997

[54] GERMICIDAL DETERGENT-IODINE COMPOSITIONS INCLUDING POLYVINYL PYRROLIDONE AND COMPATIBLE NONIONIC SURFACTANT COMPLEXORS

[75] Inventor: Murray W. Winicov, Kansas City, Mo.

[73] Assignee: West Agro, Inc., Kansas City, Mo.

[ * ] Notice: The term of this patent shall not extend beyond the expiration date of Pat. No. 5,368,868.

[21] Appl. No.: 344,925

[22] Filed: Nov. 25, 1994

Related U.S. Application Data

[63] Continuation-in-part of Ser. No. 163,596, Dec. 6, 1993, Pat. No. 5,368,868, which is a continuation of Ser. No. 947,041, Sep. 18, 1992, abandoned.

[51] Int. Cl.$^6$ ............................ A61K 33/36; A61K 31/76
[52] U.S. Cl. ...................... 424/667; 424/78.24; 514/947
[58] Field of Search ............................. 424/667, 78.24; 514/947

[56] References Cited

U.S. PATENT DOCUMENTS

| | | | |
|---|---|---|---|
| 2,706,701 | 4/1955 | Beller et al. | 525/356 |
| 2,739,922 | 3/1956 | Shelanski | 524/548 |
| 2,759,869 | 8/1956 | Sutton et al. | 424/672 |
| 2,900,305 | 8/1959 | Siggia | 524/548 |
| 3,028,299 | 4/1962 | Winicov et al. | 424/667 |
| 3,285,816 | 11/1966 | Kaplan et al. | 568/610 |
| 3,728,449 | 4/1973 | Cantor et al. | 424/667 |
| 4,022,882 | 5/1977 | Ely | 424/78.07 |
| 4,113,857 | 9/1978 | Shetty | 424/78.25 |
| 4,271,149 | 4/1983 | Winicov et al. | 424/150 |
| 4,526,751 | 7/1985 | Gartner | 424/78.25 |
| 4,684,519 | 8/1987 | Barabas | 525/358 |
| 5,368,868 | 11/1994 | Winicov | 424/667 |
| 5,409,697 | 4/1995 | Gluck | 424/78.25 |

FOREIGN PATENT DOCUMENTS

| | | |
|---|---|---|
| 2267112 | 11/1975 | France . |
| 759295 | 10/1956 | United Kingdom . |
| 8900006 | 1/1989 | WIPO . |

OTHER PUBLICATIONS

Gottardi et al., The Concentration of Free Iodine in Aqueous PVP–Iodine Containing Systems and its Variation with Temperature; Monatshefte für Chemie 117, 1011–1020 (1986).

Trubitsyna, Regulating the interaction of poly(N–vinylpyrrolidinone) with iodine. Zh. Prikl. Khim. (Leningrad) 1985, 58(3) 715–18. (Russ.).

Scheneck et al.; Some investigations on the chemistry and structure of model polyvinylpyrrolidone halogenophores; Makromol. Chem. 1980, 181(9), 1871–88 (Ger.).

Cournoyer, et al.; Interaction of poly(vinylpyrrolidinone) and iodine; J. Polym. Sci., Polym. Chem. Ed. 1974 12(3), 603–12 (Eng.).

Cavada, Poly(vinylpyrrolidinone) iodide): preparation and pharmaceutical utilization; Anales Fac. Quim. Farm., Univ. Chile. 14, 98–104 (1962).

Mizutani, Di– and polyiodides of poly(vinylpyrrolidinone); Magoya Shiritsu Daigaku Yakugakubu Kiyo 8, 80–92 (1960).

Barkin et al.; Interaction of poly(vinylpyrrolidinone); Ricerca sci. 25, Suppl., Simposio intern. chim. macromol., Milan–Turin 844–53 (1954).

Siggia, The Chemistry of poly(vinylpyrrolidinone)–iodine; J. AM. Pharm. Assoc. 46, 201–4 (1957).

Eliassaf, Interaction of poly(vinylpyrrolidone) with iodine; European Polymer J. 2(3), 269–78 (1966) (Eng.).

63–Pharmaceuticals No. 111:45369d, vol. 111, 1989.
63–Pharmaceuticals No. 116:28234s, vol. 116, 1992.
Chem. Ab. No. 117:157725x, vol. 117, 1992.
Chem. Ab. No. 117:157668f, vol. 117, 1992.
Chem. Ab., No. 11771, Vo.I. 55 (1961).
30–Pharmaceuticals, No. 13732, Vo.. 58 (1963).
Chem. Ab. No. 6616, vol. 47 (1955).
17–Pharmaceuticals, Cosmetics, Perfumes No. 21497–98, vol. 55, (1961).
35–Synthetic High Polymers No. 107:154859b; vol. 107, 1987.
Chem. Ab. No. 104:34422v; vol. 104, 1986.
63–Pharmaceuticals No. 102:31987f, vol. 102, 1985.
Chem. Ab. No. 102:32111c, vol. 102, 1985.
Chem. Ab. No. 11106d, vol. 83, 1975.
63–Pharmaceuticals No. 99:200477s, vol. 99, 1983.
Chem. Ab. No. 110:71113q, vol. 110, 198963–Pharmaceuticals No. 93:137930t, vol. 93, 1980.
46–Surface–Active Agents No. 12744x, vol. 83, 1975.
Chem. Ab. No. 40643j, vol. 71, 1969.

(List continued on next page.)

Primary Examiner—Kevin E. Weddington
Attorney, Agent, or Firm—Hovey, Williams, Timmons & Collins

[57] ABSTRACT

Stable, aqueous complexor-iodine germicidal use compositions and concentrates adapted for application to animal or human skin are provided which have desirable complexor:iodine ratios of from about 2–4.5. The compositions and concentrates preferably include a polyethoxylated polyoxypropylene block copolymer (Poloxamer) as the complexing agent, wherein the polyoxypropylene moiety has an average molecular weight of at least 2600 and a polyoxyethylene content of from about 30%–75% by weight, in combination with from about 0.1%–5% by weight average available iodine on a nominal basis. Use of the defined class of Poloxamers allows formulation of both high and low temperature stable compositions and concentrates. Other ingredients such as emollients, buffering agents and viscosity improvers can also form a part of the use compositions and concentrates. In another aspect of the invention, complexor-iodine compositions and concentrates include two-component complexor systems including individual amounts of polyvinyl pyrrolidone and a nonionic surfactant such as a Poloxamer.

43 Claims, No Drawings

OTHER PUBLICATIONS

45–Synthetic High Polymers No. 5809–10, 1964.
Chem. Ab. No. 120: 62357b, 1994.
Chem. Ab., No. 119:124987x, vol. 119, 1993.
Chem. Ab. No. 11711–72 (1961).
Chem. Ab. No. 11623–24 (1956).
Chem. Ab. No. 12787, 88– vol. 49, (1955).
63–Pharmaceuticals No. 111:45369d, 1989.
63–Pharmaceuticals No. 103:92880h, 1985.
Chem. Ab. No. 104:34422v, 1986.
C. A. Selects Antibacterial Agents No. 118:66956c, 1993.
Chem. Ab. No. 105:17835t, 1986.

GERMICIDAL DETERGENT-IODINE COMPOSITIONS INCLUDING POLYVINYL PYRROLIDONE AND COMPATIBLE NONIONIC SURFACTANT COMPLEXORS

RELATED APPLICATION

This is a continuation-in-part of Application Ser. No. 08/163,596 filed Dec. 6, 1993, now Pat. No. 5,368,868, which is a continuation of application Ser. No. 07/947,041, filed Sep. 18, 1992, now abandoned.

BACKGROUND OF THE INVENTION

1. Field of the Invention

The present invention is broadly concerned with improved, stable, complexing agent-iodine germicidal compositions and concentrates that can be diluted to provide such compositions, useful for topical applications to the skin of human or animals, having relatively low complexing agent(s)/average available iodine ratios. More particularly, it is concerned with such concentrates and use compositions wherein the complexing agent(s)/average available iodine ratio ranges from about 2:1 to about 4.5:1, and wherein the complexing agent fraction preferably comprises a polyoxypropylene-polyoxyethylene block copolymer having a central polyoxypropylene (POP) molecular weight of at least about 2600 and a polyoxyethylene (POE) content on the order of 30%–75% by weight. Use of specific complexing agents of this character has been found to yield low ratio, high and low temperature stable germicidal use compositions and concentrates. In another aspect of the invention, use compositions and concentrates are provided with from about 2–4.5 parts of a two-component complexing agent per part of available iodine, and wherein the complexing agent includes individual amounts of polyvinyl pyrrolidone (i.e. Povidone or PVP), and a compatible, nonionic, surfactant complexor, such as a polyethoxylated polyoxypropylene.

2. Description of the Prior Art

Germicidal detergent-iodine products designed for topical application to the skin have long been available. These formulations are used primarily in products such as pre-operative antiseptic preparations, hand cleaners and in bovine teat dips for mastitis prevention. Apart from complexed detergent-iodine, these products typically include variable amounts of additives to provide pH control, emolliency, viscosity, and in some cases a colorant.

It has also been known to provide Povidone-iodine germicidal compositions for topical uses. Generally, these prior compositions are characterized by relatively high levels of Povidone (e.g., a minimum of about 6:1 Povidone:iodine ratio), which have been thought necessary in order to adequately complex the iodine, particularly for human topical use products.

U.S. Pat. No. 3,728,449 describes a wide range of detergent-iodine germicidal compositions specifically adapted for application to the teats of milk animals for the control and prevention of mastitis. A number of ethoxylated nonionic iodine complexing agents are disclosed as being effective in the '449 patent, at a minimum ratio of 5 parts complexing agent to each part of average available iodine. Among the complexing agents described in this patent are the nonylphenol ethoxylates, polyalkylene glycol ethers, polyoxyethylene sorbitan monolaurate and monopalmitate, polyvinylpyrrolidone and polyethoxylated polyoxypropylenes. This latter type of complexing agent is referred to in the art as a "Poloxamer", which is a block copolymer based on a central polyoxypropylene moiety with polyoxyethylene groups at the respective ends of the central moiety. There are a wide range of commercially available Poloxamers having central moieties ranging in molecular weight from about 1000 to 4000, and containing polyoxyethylene contents on the order of 10%–80% by weight of the total weight of the Poloxamer.

In order to be dependable and useful to an end user, detergent-iodine germicidal use compositions and concentrates must be stable (i.e., remain homogeneous) over a wide range of temperature. If stability is lost, and the products separate, the utility of the compositions is significantly degraded and they can present a potential hazard to the user. Generally speaking, stability in this context means that a given product must remain homogeneous after extended storage (e.g., 1 week) at temperatures as low as 2° C. (which may be experienced in cold warehouse storage areas) or as high as 40° C., which can occur during transport in closed vehicles. Furthermore, although a given product may separate when frozen, especially after undergoing several freeze-thaw cycles, it should be readily reconstitutable as a homogeneous mixture upon simple shaking or mixing.

In addition, all detergent-iodine formulations have some iodide ion present, which can vary as desired from relatively high concentrations described in U.S. Pat. No. 3,028,299 to relatively low, stabilized values taught in U.S. Pat. No. 4,271,149. In general, iodide ion levels range from about 0.3–1 part iodide per part of iodine in prior formulations.

As indicated above, detergent-iodine products designed for topical application to the skin are normally formulated with an amount of emollient. The most common emollients employed are glycerin, lanolin and its derivatives, sorbitol, fatty acid esters of polyhydroxylated compounds, and propylene glycol. These emollients are used at levels ranging from below 1% to as much as 10% in use compositions. Glycerin is the most widely used emollient in bovine teat dips and is also used extensively at low levels in human topical povidone-iodine and deter- gent-iodine formulations.

Another desirable functional characteristic for detergent-iodine germicidal compositions designed for topical application, is the ability to spread evenly on the skin and not drain off so rapidly as to prevent insufficient germicidal contact time. Many of the usual ingredients in detergent-iodine products contribute to viscosity. However, it is common for topical products to be formulated with a specific thickener to provide added viscosity. There are many viscosity modifiers compatible with detergent-iodine systems, such as carboxymethylcellulose derivatives, polyacrylate derivatives, alginates, xanthates and polysaccharides. These are typically used at levels below 1% by weight in a final use composition. These types of ingredients, properly selected, have an insignificant effect on the homogeneity of a given use composition. On the other hand, where dilutable concentrates are desired, viscosity-modifying additives can become a problem and special care must be taken in the selection of specific agents and their levels of use in concentrates.

As explained above, the prior art is replete with examples of detergent-iodine formulations having relatively high detergent/average available iodine ratios in excess of 5:1. Patent No. 3,728,449 describes a single example at a ratio of 5:1, which makes use of PVP as a complexing agent. The next lowest ratio example in this patent uses a nonylphenol ethoxylate at a ratio of 7.5:1. Example IIID describes a composition made up to include 5 parts of a Poloxamer (Pluronic P123), but the total detergent/average available iodine ratio of this example is 8:1.

There are a number of potential advantages in the use of very low complexor/average available iodine ratios in germicidal iodine concentrates and use compositions designed for skin or tissue application. For example, in a low ratio product of this type, there would be less organic matter to react with the iodine, thereby rendering such compositions more stable relative to the labeled or nominal available iodine content. Another advantage where the principal complexor is a detergent is that reduced amounts of detergent would be expected to be less irritating to the skin and would accordingly require a lesser amount of emollient. Compositions with lower complexor/average available iodine ratios could be formulated to have higher, and more stable, free or uncomplexed iodine levels. The use of minimal amounts of complexor also would allow for the possibility of reduced water content in concentrates, thereby correspondingly reducing packaging, shipment and storage costs.

Iodine-containing compositions have also been provided in the past which include polyvinyl pyrrolidone. Such compositions, especially those conforming to U.S.P. requirements for Povidone-iodine topical solutions, have high ratios of Povidone to available iodine within the range of from about 9:1 to about 7:1. Most commercial compositions of this character also contain a small amount of surface active agent, generally about 1% or less, to lower the surface tension and thereby aid in spreading. Such a surfactant additive is frequently of the ethoxylated nonionic type, most frequently based upon a nonylphenol ethoxylate. With ratios of Povidone to iodine in the aforementioned range, the iodine complexing contribution of the small amount of nonionic surfactant employed is minimal at best.

A Poloxamer-iodine topical antiseptic ("Prepodyne") has been available for years for use in hospitals.

This composition has a Poloxamer to available iodine ratio of about 5:1, utilizing Poloxamers with an average polyoxypropylene molecular weight of around 2600. However, there are no known prior compositions containing a two-component iodine complexor comprising Povidone and a nonionic surfactant, where the total iodine complexor:iodine ratio is less than 5:1.

Accordingly, there is a real and unsatisfied need in the art for improved, low ratio complexor-iodine use compositions (and their dilutable concentrate counter-parts) which have the requisite stability and germicidal utility and which can be applied directly to animal or human skin.

SUMMARY OF THE INVENTION

The present invention overcomes the problems outlined above and provides desirable aqueous, stable, low-ratio, iodine complexed use compositions and concentrates for skin or tissue application. The present invention in one aspect is predicated upon the discovery that a certain limited class of Poloxamers can be used as a part of such low-ratio formulations without sacrificing stability or other desirable qualities.

In another aspect, the invention pertains to improved detergent-iodine use compositions and concentrates including from about 2 to about 4.5 parts of a two-component complexing agent per part of available iodine, wherein the complexing agent includes individual amounts of polyvinyl pyrrolidone and a compatible, nonionic surfactant complexor.

Generally speaking, the use compositions in accordance with the first aspect of the invention include from about 0.1%–1.3% by weight average available iodine on a nominal basis, and from about 2 to about 4.5 parts of polyethoxylated polyoxypropylene (Poloxamer) complexing agent per part of average available iodine, wherein the polyoxypropylene moiety has an average molecular weight of at least about 2,600 and a polyoxyethylene content of from about 30% to about 75% by weight. The pH of the use compositions is adjusted to a level of from about 2–7.

In preferred forms, the Poloxamer is selected such that the polyoxypropylene moiety thereof has an average molecular weight of from about 2,600–4,000, and more preferably from about 3,000–4,000, whereas the polyoxyethylene content may range from about 30% to about 75% by weight for certain types of compositions, and from about 30%–50% by weight, or 30%–40% by weight, for other types of compositions within the scope of the invention. The pH of the aqueous use compositions is advantageously from about 2–6.5, and may be in the range of from about 2–4 or 4–6.5, depending upon the composition in question; generally, lower pHs give more stable compositions. The compositions should also contain from about 0.2–1, and more preferably from about 0.3–0.5, parts iodide per part of available iodine.

The compositions of the first aspect of the invention may also include a number of other ingredients, for example an emollient which would typically be present at a level from about 0.1%–10% by weight, and more preferably from about 1%–5% by weight. Suitable emollients may be selected from the group consisting of glycerin, sorbitol, propylene glycol, lanolin, ethoxylated lanolin derivatives, and mixtures thereof. Likewise, a buffering agent such as those selected from the group consisting of the salts of citric, lactic, acetic and phosphoric acids and mixtures thereof would also normally be present for pH control, typically at a level from about 0.1%–1% by weight, and more preferably from about 0.2%–0.5% by weight.

The first aspect of the invention also comprehends aqueous germicidal concentrates adapted for dilution with water to form a resultant use composition. In such a case, the concentrate would comprise from about 1%–5% by weight average available iodine on a nominal basis, and from about 2–4.5 parts of Poloxamer complexing agent of the type described above per part of average available iodine. Other variable constituents of the concentrate would correspond, in appropriately higher amounts, to those described above in connection with the final use compositions.

The compositions of this invention are unique in that they represent the most efficient iodine complexors-solubilizers ever described. There are no other known organic substances, of any type, that can solubilize iodine at such low complexor/iodine ratios in compositions suitable for application to skin tissue. Indeed, the only substance that is somewhat more efficient at solubilizing iodine on a weight basis, is iodide ion (I) itself. As little as about 1:1 iodide/iodine can be used to solubilize iodine in water, such as the well known 2% Iodine Topical Solution (USP), but such preparations are of little practical use today, in that they are regarded as being too irritating to skin tissue.

In the second aspect of the invention, complexor-iodine use compositions and concentrates likewise contain from about 2 to about 4.5 parts of complexing agent per part of available iodine; in this case, however, the complexing agent is made up of a combination of individual amounts of polyvinyl pyrrolidone and a compatible, nonionic surfactant complexor.

In more detail, the two-component complexor use compositions and concentrates of the invention are formulated with from about 0.5 to about 4 parts of polyvinyl pyrrolidone per part of available iodine, and more preferably from about 0.5 to about 2.5 parts of PVP. Correspondingly, the level of surfactant complexor broadly ranges from about 0.5 to about 4 parts per part of available iodine, and more preferably from about 0.5 to about 3.5 parts, and most preferably from about 2 to about 3.5 parts.

The PVP fraction of the two-component complexor should have a molecular weight of from about 8,000 to about 1,300,000, which includes the commercially available materials designated as K-17, K-30, K-60 and K-90. The K-30 PVP is the most preferred member of this class.

The surfactant complexor fraction of the two-component complexing agent is preferably selected from the group consisting of the polyethoxylated polyoxypropylene, alkylphenol ethoxylates (e.g., Nonoxynols) and ethoxylated fatty alcohols and fatty acids. The polyethoxylated polyoxypropylenes are the most preferred surfactant, and the Poloxamers described above in connection with the first aspect of the invention are likewise the most preferred surfactants for use in the two-component complexing agents. Nonoxynol 10 and 15 are especially preferred surfactants. The ethoxylated fatty alcohol surfactants include the Pareth-25-9 and Pareth-25-12 surfactants (ethoxylated $C_{12}$ to $C_{15}$ fatty alcohols).

The pH of the two-component complexing agent compositions typically range from about 2 to about 7, more preferably from about 2 to about 6.5, and most preferably from about 4 to about 6.5. In the case of the corresponding concentrates, the preferred pH range is from about 3 to about 6.5.

The two-component complexor compositions and concentrates also include iodide ion, generally used at a level of from about 0.2 to 1 part iodide ion per part of available iodide, and more preferably from about 0.3 to 0.5 parts of iodide ion. Moreover, the compositions and concentrates in accordance with this aspect of the invention may include buffering agents (e.g., salts of citric, lactic, acetic, and phosphoric acids and mixtures thereof); emollient (e.g., glycerin, sorbitol, propylene glycol, lanolin, ethoxylated lanolin derivatives and mixtures thereof at a level of from about 0.1% to 15% by weight in use compositions (more preferably about 1–5%) and up to about 32% by weight (more preferably from about 0.5% to about 50% by weight in concentrates) and various other optional ingredients.

DETAILED DESCRIPTION OF THE PREFERRED EMBODIMENTS

The preferred Poloxamers useful in both aspects of the invention can be derived from any commercial source. However, the appropriate "Pluronic" Poloxamers commercialized by BASF Chemical Co. have been found to be particularly suitable, so long as members of this family are selected having the requisite polyoxypropylene molecular weight (POP Mol. Wt.) and polyoxyethylene content (POE By Wt.). Pluronic Poloxamers are described in a BASF brochure entitled "Typical Properties of Block Copolymer Surfactants", such brochure being incorporated by reference herein. It should be understood in this respect that Poloxamers having a POP molecular weight above about 4500 are not presently available, but that such species would be expected to be useful in the context of the present invention. Not every member of the defined class of Poloxamers of the present invention is necessarily suitable for every low ratio Poloxamer to average available iodine, at every iodine level. Generally speaking, with end use compositions, a somewhat higher ratio of Poloxamer to average available iodine is required at the 0.1% available iodine level, as compared with the minimal ratios required at higher available iodine levels. However, all members of this defined class which have been studied can be used at some ratio at about 4.5:1 or below. Finally, use can be made of other types of complexing agents in combination with one or more members of the defined class of Poloxamers. For example, complexing agents such as alcohol ethoxylates, nonylphenol ethoxylates, and polyvinylpyrrolidone can be used in conjunction with the defined Poloxamers, particularly where the latter are present as the major complexor component.

Furthermore, it will be understood that most detergent-iodine compositions formulated for skin application may contain a minimum of about 0.1% available iodine and a maximum of about 1.3% available iodine, and usually this maximum can be considered to be on the order of about 1% available iodine. There are detergent-iodine compositions, which have nominal available iodine values, but in fact contain significantly more average available iodine. For example, a nominal 1% available iodine product may in fact contain as much as 1.2% or even 1.25% by weight available iodine. This occurs because many compositions will contain a significant "overage" of available iodine when manufactured, so as to allow for iodine loss over the life of the product. As such, it will be understood that reference herein to average available iodine on a nominal basis covers such excess amounts.

The compositions of the invention will also contain iodide which can usually vary depending on the formulation, from about 0.2–1 part of iodide ion per part of average available iodine. However, the novel compositions of the invention are not iodide dependent insofar as the amount of iodide is concerned. The amount of iodide present can in some cases have an effect on the stability and homogeneity of a given use composition. However, the novel complexor:iodide ratios can accommodate the levels of iodide previously utilized in the art.

The presence of buffering agent(s) is generally desirable in compositions and concentrates in accordance with the present invention, and those salts described previously are preferred. Sodium citrate is the most preferred buffering agent. The amount of buffering agent employed in a particular formulation is chosen on the basis of pH stability characteristics determined over a period of time. In use compositions, the small amount of buffering agent present has little or no effect on product homogeneity and stability. In concentrates, however, where the buffering agents are present at higher levels and the water content is significantly lower, the choice of buffering agent can make a significant difference.

The compositions of the invention can also include viscosity agents commonly employed in prior formulations. Here again, the selection and amount of such agent(s) is dependent upon the particular characteristics desired for a given formulation, and whether the composition is in dilute form for end use, or is sold as a concentrate.

The compositions of the invention can also include small amounts of solvents such as alcohols and glycols, which can function to modify viscosity and to aid in the preparation of concentrates.

The following examples describe certain preferred compositions and concentrates in accordance with the first aspect of the invention, as well as methods of preparing and stability testing these formulations. It should be understood that the examples are provided by way of illustration only, and nothing therein should be taken as a limitation upon the overall scope of the invention.

EXAMPLE 1

A series of aqueous detergent-iodine compositions in accordance with the invention were prepared, each including 4.5% by weight of a Poloxamer, an average available iodine content of about 1% (thereby giving a Poloxamer:available iodine ratio of 4.5), 0.4% by weight iodide, 2.0% by weight glycerin, and 0.5% by weight sodium citrate buffer to give an adjusted pH of about 5. The balance of the compositions was made up of water. In some samples, the Poloxamer used had proper molecular weight and percentage polyoxyethylene values in accordance with the invention, and in other samples, different types of Poloxamers were used.

Each sample was prepared by mixing an appropriate commercial Pluronic Poloxamer (or a mixture of commercial grades to achieve intermediate value Poloxamers) with an aqueous iodine concentrate containing approximately 57% by weight iodine and 20% by weight iodide as sodium iodide. A small amount of water was then added followed by the glycerin and sodium citrate buffer. After a small amount of mixing, the remaining formula amount of water was added. After formulation, the homogeneity of the compositions was observed at room temperature, and portions of each sample were tested for high and low temperature stability. Specifically, in the low temperature stability test, the respective samples were placed in a refrigerator at 2° C. for one week, and in the high temperature test, the samples were placed in a constant temperature 40° C oven. At the end of the test week, both low and high temperature test samples were observed for precipitation and cloudiness; any exhibiting undue cloudiness or precipitation were rejected.

The following Table 1 sets forth the Poloxamer molecular weight and percentage polyoxyethylene for the test samples, as well as the results of the stability tests, where "O.K." represents an acceptable product and "X" represents an unacceptable product.

TABLE 1

| Sample # | POP Mol. Wt.[1] | POE %[2] | Stability |
| --- | --- | --- | --- |
| 1 | 2600 | 50 | O.K. |
| 2 | 3200 | 30 | O.K. |
| 3 | 3200 | 40 | O.K. |
| 4 | 3200 | 50 | O.K. |
| 5 | 4000 | 30 | O.K. |
| 6 | 4000 | 70 | O.K. |
| 7 | 1300 | 40 | X |
| 8 | 1700 | 20 | X |
| 9 | 1700 | 40 | X |
| 10 | 1700 | 50 | X |
| 11 | 1700 | 80 | X |
| 12 | 2100 | 50 | X |
| 13 | 2300 | 40 | X |
| 14 | 2300 | 50 | X |
| 15 | 2300 | 70 | X |

[1]POP Mol. Wt. = the average molecular weight of the central polyoxypropylene group of the Poloxamer block copolymer
[2]POE % = the average polyoxyethylene content of the Poloxamer block copolymer, based upon total weight of the copolymer, i.e., 50% = about 50% by weight of the total Poloxamer constitutes POE The above data demonstrates that the an average POP molecular weight on the order of about 2500 up to about 4000, together with a POE content of from about 25%–75% by weight, is important in obtaining a stable product having a relatively low Poloxamer:available iodine ratio.

EXAMPLE 2

In another series of similar tests, aqueous detergent-iodine compositions were prepared having varying compositions with different levels of Poloxamer, emollient, and pH, and the above-described stability tests were performed. Each sample contained an appropriate Poloxamer, an average available iodine content of about 1.0%, and 0.5% by weight sodium citrate buffer; the samples were made by the steps outlined in Example 1, and the balance of each composition was water. The results of these tests are set forth in Table 2.

TABLE 2

| Sample # | POP Mol. Wt. | POE % | Wt. % Poloxamer | Iodide | Glycerin % By Wt. | pH | Stability |
| --- | --- | --- | --- | --- | --- | --- | --- |
| 1 | 3200 | 50 | 4.5 | 0.4 | 2 | 3 | O.K. |
| 2 | 3200 | 50 | 4.5 | 0.4 | 2 | 4 | O.K. |
| 3 | 3200 | 50 | 4.5 | 0.4 | 10 | 5 | O.K. |
| 4 | 3200 | 50 | 2.5 | 0.4 | 0 | 5 | O.K. |
| 5 | 3200 | 50 | 2.5 | 0.4 | 5 | 5 | O.K. |
| 6 | 3200 | 50 | 2.5 | 0.4 | 2 | 5 | O.K. |
| 7 | 3200 | 40 | 4.5 | 0.4 | 2 | 6 | O.K. |
| 8 | 3200 | 40 | 4.5 | 0.4 | 2 | 7 | O.K. |
| 9 | 3200 | 40 | 3.5 | 0.4 | 0 | 5 | O.K. |
| 10 | 3200 | 30 | 3.0 | 0.4 | 5 | 5 | O.K. |
| 11 | 3200 | 50 | 4.5 | 1.0 | 10 | 5 | O.K. |

This example demonstrates that emollient content, iodide and pH levels can be varied over wide ranges, while still providing acceptable compositions having low detergent-iodine ratios.

EXAMPLE 3

In this test, a number of aqueous detergent-iodine compositions were prepared and stability tested as set forth in Example 1. In each case, the Poloxamer had a POP mol. wt. of 3200, and a POE content of 50% (except Sample #2 which had a POE content of 40%); all had an average available iodine content of 0.5% by weight, an iodide content of 0.2% by weight, a sodium citrate content of 0.25% by weight, and a pH of about 5. The amounts of Poloxamer and glycerin were varied, but in all cases, the balance of the respective compositions was made up of water. These results are set forth below.

TABLE 3

| Sample # | Wt. % Poloxamer | Poloxamer/Av. $I_2$ | Glycerin % By Wt. | Stability |
| --- | --- | --- | --- | --- |
| 1 | 1.25 | 2.5 | 2 | O.K. |
| 2 | 1.25 | 2.5 | 2 | O.K. |
| 3 | 1.0 | 2.0 | 5.0 | O.K. |
| 4 | 1.0 | 2.0 | 10 | O.K. |

EXAMPLE 4

A further series of compositions were prepared and stability tested, using various commercial grade Poloxamers (or mixtures thereof) at different levels, with an average iodine content of about 0.25% by weight, 0.2% by weight sodium citrate buffer and with a pH of about 5. The compositions were made and tested as in Example 1 and the balance of each composition was water. The data from this test series is set forth in Table 4.

TABLE 4

| Sample # | POP Mol. Wt. | POE % Wt. | Wt. % Poloxamer | Poloxamer/Av. $I_2$ | Iodide % By Wt. | Glycerin % By Wt. | Stability |
| --- | --- | --- | --- | --- | --- | --- | --- |
| 1 | 3200 | 50 | 0.625 | 2.5 | 0.1 | 1 | O.K. |
| 2 | 4000 | 30 | 0.625 | 2.5 | 0.1 | 1 | O.K. |
| 3 | 3200 | 50 | 0.5 | 2.0 | 0.1 | 10 | O.K. |
| 4 | 4000 | 30 | 0.5 | 2.0 | 0.1 | 10 | O.K. |
| 5 | 4000 | 30 | 0.625 | 2.5 | 0.25 | 1 | O.K. |

EXAMPLE 5

In this example, a series of low ratio, pH =5 aqueous Poloxamer detergent-iodine compositions containing 0.25% by weight average available iodine and 0.2% by weight sodium citrate buffer were prepared and stability tested as set forth in Example 1; the balance of all compositions was water. The results are set forth in the following table, and should be compared with the results of Table 4.

TABLE 5

| Sample # | POP Mol. Wt. | POE % Wt. | Wt. % Poloxamer | Poloxamer/Av. $I_2$ | Iodide % By Wt. | Glycerin % By Wt. | Stability |
| --- | --- | --- | --- | --- | --- | --- | --- |
| 1 | 2300 | 50 | 0.625 | 2.5 | 0.1 | 1 | X |
| 2 | 2300 | 50 | 1.0 | 4 | 0.1 | 1 | X |
| 3 | 2300 | 50 | 1.125 | 4.5 | 0.1 | 10 | X |
| 4 | 1700 | 50 | 1.0 | 4 | 0.1 | 1.0 | X |

As set forth above, the approximate 0.25% available iodine compositions having POP molecular weights of less than about 2600 were unsatisfactory, whereas those compositions set forth in Table 4 made with higher molecular weight POP moieties were stable.

EXAMPLE 6

Another series of compositions were prepared, all having 0.45% by weight Poloxamer, an available iodine content of about 0.1% by weight, an iodide content of about 0.04% by weight and a pH of about 5. These compositions were made and tested as set forth in Example 1, with the balance of each composition being water.

TABLE 6

| Sample # | POP Mol. Wt. | POE % By Wt. | Poloxamer/ Av. $I_2$ | Glycerin % By Wt. | Sodium Citrate % By Wt. | Stability |
| --- | --- | --- | --- | --- | --- | --- |
| 1 | 3200 | 50 | 4.5 | — | 0.1 | O.K. |
| 2 | 3200 | 50 | 4.5 | 1 | 0.1 | O.K. |
| 3 | 4000 | 30 | 4.5 | 2 | 0.1 | O.K. |
| 4 | 4000 | 50 | 4.5 | — | 0.1 | O.K. |
| 5 | 4000 | 50 | 4.5 | 5 | 0.1 | O.K. |
| 6 | 3200 | 50 | 4.5 | — | 0.05 | O.K. |

EXAMPLE 7

A series of aqueous detergent-iodine compositions were made using a number of different Poloxamers all having POP molecular weights below 2600. In all cases, 0.45% by weight Poloxamer was used, and the compositions contained about 0.1% by weight available iodine, 0.04% by weight iodide, 0.2% by weight glycerin and 0.05% by weight sodium citrate; all compositions had a pH of 5. All of the compositions were unstable either at room temperature or at cooler temperatures. In this series of compositions, Poloxamers having the following POP molecular weight/POE percentage distributions were used: 1300/40%; 1700/20%; 1700/40%; 1700/50%; 1700/80%; 2100/50%; 2300/40; and 2300/70%.

EXAMPLE 8

As described previously, the iodine concentration of iodine compositions adapted for topical application to the skin is predominantly in the range of from about 0.1%–1% average available iodine. It is frequently desired to make concentrates of such compositions, suitable for dilution prior to use. Such concentrates offer the advantages of minimizing manufacturing, packaging, shipping and storage costs. The detergent-iodine compositions of the invention are particularly suited for such concentrates, since they use a minimum total solids in the concentrate and therefore maximize the amount of water that can be present. Without sufficient water, many concentrates are excessively viscous, and it may be difficult to provide proper pH buffering.

Generally speaking, concentrates usually contain from about 1%–5% by weight of available iodine, and are usually formulated to provide 4,8 and 16 times the original concentrate volume, after dilution with an appropriate amount of water.

A composition adapted for dilution with 3 parts of water to yield a 1% available iodine level can be formulated using a Poloxamer having a POP mol. wt./POE % by weight value of 3200/50% at a level of 12%; 4.3% by weight average available iodine; an iodide content of 1.5% by weight and a pH 3 citrate buffer content of 0.5% by weight. These compositions are formulated as set forth in Example 1.

Another composition for use at the same 1+3 dilution factor to yield a 1% nominal available iodine level, can be formulated using a Poloxamer having a POP mol. wt./POE % by weight value of 3200/54% at a level of 16%; 4.1% by weight average available iodine; an iodide content of 1.4% by weight; 19% by weight glycerin; and a pH 5 citrate buffer content of 0.5% by weight. The balance of this composition is water.

The following compositions shown below can be diluted with 7 and 15 parts of water to yield 0.1% average available iodine. The compositions are prepared as set forth in Example 1, and the balance thereof in each case is water.

TABLE 8

| Sample # | POP Mol. Wt. | POE % Wt. | Wt. % Poloxamer | Ratio | Av. $I_2$ | Iodide % By Wt. | Glycerin % By Wt. | Sodium Citrate Buffer | pH |
|---|---|---|---|---|---|---|---|---|---|
| 1 | 3200 | 50 | 3.6 | 4.5 | 0.8 | 0.32 | — | 0.8 | 5 |
| 2 | 3200 | 50 | 3.6 | 4.5 | 0.8 | 0.32 | 8 | 0.8 | 5 |
| 3 | 4000 | 30 | 3.6 | 3.5 | 0.8 | 0.32 | 16 | 0.8 | 5 |
| 4 | 3200 | 50 | 7.2 | 4.5 | 1.6 | 0.64 | 16 | 1.6 | 5 |
| 5 | 3200 | 50 | 7.2 | 4.5 | 1.6 | 0.64 | — | 1.6 | 5 |

As can be seen from the foregoing examples, the present invention provides stable, improved Poloxamer iodine germicidal use compositions and concentrates of varying makeup. The following tables respectively for the use compositions and concentrates set forth the types of ingredients contemplated in connection with the first aspect of the invention, as well as approximate ranges and preferred use levels thereof.

TABLE 9

Use Compositions

| Ingredients | Broad Range | Preferred Range |
|---|---|---|
| 1. Parts Poloxamer per Part Available $I_2$ | 2–4.5 | 2.5–4.5 |
|   a. POP Mol. Wt. | ≧2600 | 3200–4000 |
|   b. POE % By Wt. | 30–75 | 40–70 |
| 2. Average Available $I_2$ % By Weight | 0.1–1.3 | 0.1–1 |
| 3. Parts Iodide Per Part Available $I_2$ | 0.2–1 | 0.3–0.5 |
| 4. Emollient % By Wt. | 0–10 | 1–5 |
| 5. Buffering Agent % By Wt. | 0.1–1 | 0.2–0.5 |
| 6. Water % By Wt. | q.s.* | q.s.* |
| 7. pH | 2–7 | 4–6.5 |

*Quantity Sufficient to bring total to 100%.

TABLE 10

Concentrates

| Ingredients | Broad Range | Preferred Range |
|---|---|---|
| 1. Parts Poloxamer per Part Available $I_2$ | 2–4.5 | 2.5–4.5 |
|   a. POP Mol. Wt. | ≧2600 | 3200–4000 |
|   b. POE % By Wt. | 30–75 | 40–70 |
| 2. Average Available $I_2$ % By Wt. | 1–5 | — |
| 3. Parts Iodide Per Part Available $I_2$ | ≧0.2 | 0.3–0.5 |
| 4. Emollient % By Wt. | 0–32 | 8–16 |
| 5. Buffering Agent % By Wy. | 0.2–2 | 0.5–1.5 |
| 6. Water % By Wt. | q.s.* | q.s.* |
| 7. pH | 2–7 | 3–6.5 |

*Quantity Sufficient to bring total to 100%

The following examples describe various complex-or iodine compositions including two-component complexing agents containing Povidone and nonionic surfactant. It is to be understood that these examples are provided by way of illustration only, and nothing therein should be taken as a limitation upon the overall scope of the invention.

In these examples, various trade designations for some of the ingredients are employed, e.g., Poloxamer, Povidone, Nonoxynol and Pareth, with subsequent identifying numbers. These identifications are well known in the art, and further information can be obtained from various standard sources, such as The CTFA Cosmetic Ingredient Dictionary.

EXAMPLE 9

A series of aqueous combinations of Povidone K-30 and a nonionic surfactant complexor, with iodine, was prepared. The ratio of Povidone to available (thiosulfate titratable) iodine ranged from 0.5:1 to 1.5:1, the ratio of nonionic surfactant (Poloxamer 335) to available iodine ranged from 1.5:1 to 0.5:1. The samples were prepared by first dissolving the required amount of nonionic surfactant complexor in or about 50% of the required amount of water, followed by the addition, with stirring, of an aqueous iodine concentrate containing approximately 57% by weight iodine and 24% by weight sodium iodide. The required amount of Povidone powder was then added, with stirring. The emollient, glycerin, was added next followed by the citric acid and the appropriate amount of sodium hydroxide solution, to reach the desired, buffered pH level. The remaining formula amount of water was then added, with stirring. Finally, the preparations were filtered.

TABLE 11

| | Composition | | |
|---|---|---|---|
| Ingredient (% by wt) | 1 | 2 | 3 |
| Poloxamer 335 | 1.5 | 1 | 0.5 |
| Povidone K-30 | 0.5 | 1 | 1.5 |
| Available Iodine | 1 | 1 | 1 |
| Glycerin | 8 | 6 | 4 |
| Citric Acid | 0.1 | 0.1 | 0.1 |
| pH | ~5 | ~5 | ~5 |
| Water | q.s. 100% | q.s. 100% | q.s. 100% |

EXAMPLE 10

A series of aqueous compositions containing Povidone, nonionic surfactants and iodine was prepared with ratios of Povidone:iodine of 2.5:1 and nonionic surfactant:iodine of 2:1. All compositions were tested for homogeneity/stability for at least one week at 2° C. (refrigerator) and at 40° C. in a constant temperature oven; any compositions exhibiting undue cloudiness or precipitation were rejected. However, all of the compositions of Table 2 were satisfactory.

TABLE 12

| Ingredient (% by wt) | Composition | | | | | | | | |
|---|---|---|---|---|---|---|---|---|---|
| | 4 | 5 | 6 | 7 | 8 | 9 | 10 | 11 | 12 |
| K-30 Povidone | 2.5 | 2.5 | 2.5 | 2.5 | 2.5 | 2.5 | 2.5 | 2.5 | 2.5 |
| Poloxamer 185 | 2 | — | — | — | — | — | — | — | — |
| Poloxamer 188 | — | 2 | — | — | — | — | — | — | — |
| Poloxamer 335 | — | — | 2 | — | — | — | — | — | — |
| Poloxamer 403 | — | — | — | 2 | — | — | — | — | — |
| Poloxamer 407 | — | — | — | — | 2 | — | — | — | — |
| Nonoxynol 10 | — | — | — | — | — | 2 | — | — | — |
| Nonoxynol 15 | — | — | — | — | — | — | 2 | — | — |
| Pareth-25-9 | — | — | — | — | — | — | — | 2 | — |
| Pareth-25-12 | — | 1' | — | — | — | — | — | — | 2 |
| Available Iodine | 1 | 1 | 1 | 1 | 1 | 1 | 1 | 1 | 1 |
| Citric Acid | 0.1 | 0.1 | 0.1 | 0.1 | 0.1 | 0.1 | 0.1 | 0.1 | 0.1 |
| pH | –5 | –5 | –5 | –5 | –5 | –5 | –5 | –5 | –5 |
| Water | q.s. 100% | q.s. 100% | q.s. 100% | q.s. 100% | q.s. 100% | q.s. 100% | q.s. 100% | q.s. 100% | q.s. 100% |

Similar compositions were prepared using Povidone with K-values of 17,60 and 90, and gave homogenous products. Substantially all aqueous dilutions of these compositions gave homogeneous end products that were not cloudy and did not separate. The approximate average molecular weights for Povidone with K-values of 17,30,60 and 90 are 9,000; 42,000; 200,000; and 1,100,000, respectively.

In a similar fashion, compositions 13–22 were prepared as outlined above, using all of the ingredients of Table 12, except that Poloxamer 235 was used, and Poloxamer 334 was used in lieu of Poloxamer 335. However, the total amount of nonionic surfactant complexor used in each case was 0.5% by weight, rather than the 2% level of Table 12.

EXAMPLE 11

A series of compositions was prepared containing 2.5% Povidone of different K-values, together with a nonionic surfactant co-complexor and glycerin emollient. The ingredients of these compositions are set forth in Table 13. The iodide levels of the compositions were approximately 0.4% by weight.

TABLE 13

| Ingredient (% by wt) | Composition | | | | | | | |
|---|---|---|---|---|---|---|---|---|
| | 23 | 24 | 25 | 26 | 27 | 28 | 29 | 30 |
| Povidone K-17 | 2.5 | — | — | — | 2.5 | — | — | — |
| Povidone K-30 | — | 2.5 | — | — | — | 2.5 | — | — |
| Povidone K-60 | — | — | 2.5 | — | — | — | 2.5 | — |
| Povidone K-90 | — | — | — | 2.5 | — | — | — | 2.5 |
| Available Iodine | 1 | 1 | 1 | 1 | 1 | 1 | 1 | 1 |
| Poloxamer 335 | 0.5 | 0.5 | 0.5 | 0.5 | 2 | 2 | 2 | 2 |
| Glycerin | 2 | 2 | 2 | 2 | 2 | 2 | 2 | 2 |
| Citric Acid | .1 | .1 | .1 | .1 | .1 | .1 | .1 | .1 |
| pH | 5–6 | 5–6 | 5–6 | 5–6 | 5–6 | 5–6 | 5–6 | 5–6 |
| Water | q.s. 100% | q.s. 100% | q.s. 100% | q.s. 100% | q.s. 100% | q.s. 100% | q.s. 100% | q.s. 100% |

Compositions 13–22 were also stable at high and low temperatures.

Variants of compositions 13–22 were also prepared using povidone with K-values of 17,60 and 90. These variants also gave homogeneous products, and their aqueous dilutions generally gave homogeneous solutions that were not cloudy and did not separate.

EXAMPLE 12

A series of compositions was prepared containing 2% Povidone K-30 together with either 0.5% or 1% by weight co-complexor nonionic surfactant. All of the compositions contained citrate buffer and an iodide content of about 0.4-0.5 parts per one part of available iodine, together with some glycerin. The following are examples of homogeneous compositions.

TABLE 14

| Ingredient (% by wt) | Compositions | | | | | | |
|---|---|---|---|---|---|---|---|
| | 31 | 32 | 33 | 34 | 35 | 36 | 37 |
| Povidone K-30 | 2 | 2 | 2 | 2 | 2 | 2 | 2 |
| Poloxamer 333 | 0.5 | — | — | — | — | — | — |
| Poloxamer 334 | — | 0.5 | — | — | — | — | — |
| Poloxamer 335 | — | — | 0.5 | — | 1 | — | — |
| Poloxamer 403 | — | — | — | 0.5 | — | 1 | — |
| Pareth-25-12 | — | — | — | — | — | — | 1 |
| Available Iodine | 1 | 1 | 1 | 1 | 1 | 1 | 1 |
| Glycerin | 2 | 2 | 2 | 2 | 2 | 2 | 2 |
| Citric Acid | 0.25 | 0.25 | 0.25 | 0.25 | 0.25 | 0.25 | 0.25 |
| pH | ~5 | ~5 | ~5 | ~5 | ~5 | ~5 | ~5 |
| Water | q.s. 100% | q.s. 100% | q.s. 100% | q.s. 100% | q.s. 100% | q.s. 100% | q.s. 100% |

EXAMPLE 13

In this example, compositions 38 and 39 were prepared each containing in percent by weight: 1% Povidone K-30; 1% available iodine; 2% glycerin; 0.2% citric acid and water q.s. 100%. The compositions each had a pH of about 5 and differed in the nonionic surfactant complexor used. In the case of composition 38, Poloxamer 335 was used at a level of 1.5%, whereas in composition 39, Poloxamer 403 was employed at that same level. At these complexor ratios, use of Poloxamers having a central hydrophobic moiety of a molecular weight greater than about 3,000 is preferred.

EXAMPLE 14

In this example, additional 1% iodine compositions Nos. 40 and 41 were prepared using 0.5% K-30 Povidone (0.5:1 ratio) in combination with 4% nonionic surfactant co-complexor (4:1 ratio) based on Poloxamers having a central moiety molecular weight of about 3,000 or more, together with from about 30–50% ethylene oxide content. At a 4:1 ratio of nonionic surfactant co-complexor to iodine, these Poloxamers functioned better than most other nonionic surfactants.

Each of the compositions of this example contained (% by weight): Povidone K-30, 0.5%; available iodine, 1%; glycerin, 2%; citric acid, 0.1%; and water, q.s. 100%. Each of the compositions had a pH of around 5. In the case of composition 40, 4% of Poloxamer 335 was used, whereas in composition 41, the same level of Poloxamer 403 was employed.

EXAMPLE 15

Two bovine teat dips were prepared in accordance with the present invention. These dips had an available iodine content of about 0.15% and relatively high levels of emollient (glycerin and sorbitol). At such low iodine contents and high organic emollient contents, iodine stability can be maintained through the use of the iodate technology described in U.S. Pat. No. 4,271,149, which is incorporated by reference herein. In such teat dips, it is customary to employ a viscosity agent to thicken the product so that it does not drain off too rapidly. Also, use of a small amount of effective wetting agent can further aid uniform spreading and adhesion.

Each of the teat dip compositions 42 and 43 contained the following ingredients (% by weight): povidone K-30, 0.3%; available iodine, 0.15%; glycerin, 2%; 70% sorbitol, 3%; citric acid, 0.1%; xanthan gum thickener, 0.1%; dioctyl sodium sulfosuccinate, 0.04%; sodium iodate, 0.12%; and water, q.s. 100%. The compositions had a pH of 5–6. Teat dip composition 42 contained 0.375% Poloxamer 403, and composition 43 contained the same amount of Pareth-25-12.

Compositions made in accordance with this example provide a free (uncomplexed) iodine content in the range of about 5–10 ppm, resulting in very fast germicidal activity. The xanthan gum provides a viscosity of about 30 cps, resulting in good adherence. The 4% total emollient content provides excellent skin conditioning characteristics, considering that this represents more than 80% of the total solid ingredient content.

EXAMPLE 16

A series of iodine compositions containing Povidone K-30 and various nonionic surfactant complexors was prepared, in which the total complexor:iodine ratio was 2.5:1. These compositions were prepared as described in Example 9, with some of the compositions containing additional ingredients to modify viscosity and wetting characteristics. The ingredients of these compositions are set forth below.

TABLE 15

| Ingredient (% by wt.) | Composition | | | | | | | | | | | | |
|---|---|---|---|---|---|---|---|---|---|---|---|---|---|
| | 44 | 45 | 46 | 47 | 48 | 49 | 50 | 51 | 52 | 53 | 54 | 55 | 56 |
| Povidone K-30 | 0.5 | 0.5 | 0.5 | 2.0 | 2.0 | 2.0 | 2.0 | 2.0 | 2.0 | 2.0 | 2.0 | 2.0 | 2.0 |
| Available Iodine | 1 | 1 | 1 | 1 | 1 | 1 | 1 | 1 | 1 | 1 | 1 | 1 | 1 |
| Glycerin | 2 | 2 | 2 | 2 | 2 | 2 | 2 | 2 | 2 | 2 | 2 | 2 | 2 |
| Citric Acid | 0.25 | 0.25 | 0.25 | 0.25 | 0.25 | 0.25 | 0.25 | 0.25 | 0.25 | 0.25 | 0.25 | 0.25 | 0.25 |
| Hydroxyethylcellulose | — | — | — | 0.2 | 0.2 | 0.2 | 0.2 | 0.2 | 0.2 | — | — | — | — |
| Dioctyl Sodium Sulfosuccinate | — | — | — | 0.04 | 0.04 | 0.04 | 0.04 | 0.04 | 0.04 | — | — | — | — |

TABLE 15-continued

| Ingredient (% by wt.) | Composition | | | | | | | | | | | | |
|---|---|---|---|---|---|---|---|---|---|---|---|---|---|
| | 44 | 45 | 46 | 47 | 48 | 49 | 50 | 51 | 52 | 53 | 54 | 55 | 56 |
| Caustic Soda to pH | ~5 | ~5 | ~5 | ~5 | ~5 | ~5 | ~5 | ~5 | ~5 | ~5 | ~5 | ~5 | ~5 |
| Poloxamer 334 | 2.0 | — | — | — | 0.5 | — | — | — | — | — | 0.5 | — | — |
| Poloxamer 335 | — | 2.0 | — | — | — | 0.5 | — | — | — | — | — | 0.5 | — |
| Poloxamer 403 | — | — | 2.0 | — | — | — | 0.5 | — | — | — | — | — | 0.5 |
| Poloxamer 188 | — | — | — | 0.5 | — | — | — | — | — | — | — | — | — |
| Poloxamer 407 | — | — | — | — | — | — | — | 0.5 | — | — | — | — | — |
| Poloxamer 333 | — | — | — | — | — | — | — | — | — | 0.5 | — | — | — |
| Pareth 25-12 | — | — | — | — | — | — | — | — | 0.5 | — | — | — | — |
| Water | q.s. 100% | q.s. 100% | q.s. 100% | q.s. 100% | q.s. 100% | q.s. 100% | q.s. 100% | q.s. 100% | q.s. 100% | q.s. 100% | q.s. 100% | q.s. 100% | q.s. 100% |

At concentrations of 0.5% and 0.25% average available iodine, many stable compositions with similar ratios of ingredients can be prepared. At 0.1% average available iodine, with similar ratios, some stable compositions can be made.

EXAMPLE 17

In this example, a dilutable concentrate composition was prepared. Such concentrates can be provided at iodine levels higher than 1% so that upon dilution with water, a finished 1% or lower (down to about 0.05%) iodine product results. Not every formulation can be concentrated appreciably, owing to viscosity and homogeneity considerations, but a representative concentrate in accordance with the invention contains (% by weight): Povidone K-30, 6.0%; available iodine, 3%; Poloxamer 335, 3%; glycerin, 6%; citric acid; 0.25%; and water, q.s. 100%. This concentrate has a pH of about 5–6, and can be diluted in water to form a stable composition having an available iodine content of about 1%.

As can be seen from the foregoing examples, the present invention provides stable, improved, detergent-iodine use compositions and concentrates characterized by a two-component complexing systems. The following tables respectively for such use compositions and concentrates set forth the types of ingredients contemplated, as well as appropriate ranges and preferred levels of use thereof.

TABLE 16

Use Compositions Containing Two-Component Complexor Systems

| Ingredients | Broad Range | Preferred Range |
|---|---|---|
| 1. Parts Total Complexer System per Part Available $I_2$ | 2–4.5 | 2.5–4.5 |
|   a. Parts PVP per Part Available $I_2$ | 0.5–4 | 0.5–2.5 |
|   b. Parts Complexer Surfactant per Part Available $I_2$ | 0.5–4 | 2–3.5 |
| 2. Average Available $I_2$ % By Wt. | 0.1–1.3 | 0.1–1 |
| 3. Parts Iodide Per Part Available $I_2$ | 0.2–1 | 0.3–0.5 |
| 4. Emollient % By Wt. | 0.1–15 | 1–5 |
| 5. Buffering Agent % By Wt. | 0.1–1 | 0.2–0.5 |
| 6. Water % By Wt. | q.s.* | q.s.* |
| 7. pH | 2–7 | 4–6.5 |

*Quantity Sufficient to bring total to 100%.

TABLE 17

Concentrates Containing Two-Component Complexor Systems

| Ingredients | Broad Range | Preferred Range |
|---|---|---|
| 1. Parts Total Complexor System per Part Available $I_2$ | 2–4.5 | 2.5–4.5 |
|   a. Parts PVP per Part Available $I_2$ | 0.5–4 | 0.5–2.5 |
|   b. Parts Complexor Surfactant per Part Available $I_2$ | 0.5–4 | 2–3.5 |
| 2. Average Available $I_2$ % By Wt. | 1–5 | — |
| 3. Parts Iodide Per Part Available $I_2$ | 0.2–1 | 0.3–0.5 |
| 4. Emollient % By Wt. | 0.5–50 | 8–16 |
| 5. Buffering Agent % By Wt. | 0.2–2 | 0.5–1.5 |
| 6. Water % By Wt. | q.s.* | q.s.* |
| 7. pH | 2–7 | 3–6.5 |

*Quantity Sufficient to bring total to 100%

I claim:

1. An aqueous, stable, complexor-iodine germicidal composition comprising an amount of average available iodine on a nominal basis, and from about 2 to about 4.5 parts of complexing agent per part of average available iodine, said complexing agent comprising individual amounts of polyvinyl pyrrolidone and a compatible nonionic surfactant complexor, said composition having a sufficient quantity of said complexing agent to remain homogeneous after one week's storage at temperatures of 2° C. and 40° C.

2. The composition of claim 1, said available iodine being present at a level of from about 0.1% to about 1.3% by weight of available iodine on a nominal basis.

3. The composition of claim 1, said polyvinyl pyrrolidone being present at a level of from about 0.5 to about 4 parts per part of available iodine.

4. The composition of claim 3, said level being from about 0.5 to about 2.5 parts.

5. The composition of claim 1, said surfactant complexor being selected from the group consisting of the polyethoxylated polyoxypropylenes, alkylphenol ethoxylates and ethoxylated fatty alcohol and acid surfactants and mixtures thereof.

6. The composition of claim 5, said surfactant complexor being a polyethoxylated polyoxypropylene having an average polyoxypropylene molecular weight and an average polyoxyethylene content, said average polyoxypropylene molecular weight being up to about 4500.

7. The composition of claim 6, said average polyoxypropylene molecular weight being from about 2600 to about 4000.

8. The composition of claim 7, said average polyoxypropylene molecular weight being from about 3000 to about 4000.

9. The composition of claim 6, said average polyoxyethylene content being from about 30% to about 75% by weight.

10. The composition of claim 9, said average polyoxyethylene content from about 30% to about 50% by weight.

11. The composition of claim 1, said composition having a pH of from about 2 to about 7.

12. The composition of claim 11, said pH being from about 3 to about 6.5.

13. The composition of claim 11, said pH being from about 4 to about 6.5.

14. The composition of claim 1, said surfactant complexor being present at a level of from about 0.5 to about 4 parts surfactant complexor per part of available iodine.

15. The composition of claim 14, said level being from about 0.5 to about 3.5 parts.

16. The composition of claim 1, including from about 0.2 to about 1 part of iodide ion per part of available iodine.

17. The composition of claim 16, including from about 0.3 to about 0.5 part of iodide ion per part of available iodine.

18. The composition of claim 1, including a buffering agent.

19. The composition of claim 18, said buffering agent being selected from the group consisting of the salts of citric, lactic, acetic and phosphoric acids and mixtures thereof.

20. The composition of claim 1, including a quantity of emollient therein.

21. The composition of claim 20, said emollient being present at a level of from about 0.1% to about 15% by weight.

22. The composition of claim 20, said emollient being selected from the group consisting of glycerin, sorbitol, propylene glycol, lanolin, ethoxylated lanolin derivatives, and mixtures thereof.

23. An aqueous, stable, complexor-iodine germicidal concentrate adapted for dilution with water to form a stable use composition, said concentrate comprising from about 1% to about 5% by weight average available iodine on a nominal basis, and from about 2 to about 4.5 parts of complexing agent per part of available iodine, said complexing agent comprising individual amounts of polyvinyl pyrrolidone and a compatable nonionic surfactant complexor, said concentrate having a sufficient quantity of said complexing agent to remain homogeneous after one week's storage at temperatures of 2° C. and 40° C.

24. The concentrate of claim 23, said polyvinyl pyrrolidone being present at a level of from about 0.5 to about 4 parts per part of available iodine.

25. The concentrate of claim 24, said level being from about 0.5 to about 2.5 parts.

26. The concentrate of claim 23, said surfactant complexor being selected from the group consisting of the polyethoxylated polyoxypropylenes, alkylphenol ethoxylates and ethoxylated fatty alcohol and fatty acid surfactants and mixtures thereof.

27. The concentrate of claim 26, said surfactant being a polyethoxylated polyoxypropylene having an average polyoxypropylene molecular weight and an average polyoxyethylene content, said average polyoxypropylene molecular weight being up to about 4500.

28. The concentrate of claim 27, said average polyoxypropylene molecular weight being from about 2600 to about 4000.

29. The concentrate of claim 28, said average polyoxypropylene molecular weight being from about 3000 to about 4000.

30. The concentrate of claim 27, said average polyoxyethylene content being from about 30% to about 75% by weight.

31. The concentrate of claim 30, said average polyoxyethylene content from about 30% to about 50% by weight.

32. The concentrate of claim 23, said concentrate having a pH of from about 2 to about 7.

33. The concentrate of claim 32, said pH being from about 3 to about 6.5.

34. The concentrate of claim 32, said pH being from about 4 to about 6.5.

35. The concentrate of claim 23, said surfactant complexor being present at a level of from about 0.5 to about 4 parts surfactant complexor per part of available iodine.

36. The concentrate of claim 35, said level being from about 0.5 to about 3.5 parts.

37. The concentrate of claim 23, including from about 0.2 to about 1 part of iodide ion per part of available iodine.

38. The concentrate of claim 37, including from about 0.3 to about 0.5 part of iodide ion per part of available iodine.

39. The concentrate of claim 23, including a buffering agent.

40. The concentrate of claim 39, said buffering agent being selected from the group consisting of the salts of citric, lactic, acetic and phosphoric acids and mixtures thereof.

41. The concentrate of claim 23, including a quantity of emollient therein.

42. The concentrate of claim 41, said emollient being present at a level of from about 0.5% to about 50% by weight.

43. The concentrate of claim 41, said emollient being selected from the group consisting of glycerin, sorbitol, propylene glycol, lanolin, ethoxylated lanolin derivatives, and mixtures thereof.

\* \* \* \* \*